United States Patent [19]
Venkatesan et al.

[11] Patent Number: 5,594,152
[45] Date of Patent: Jan. 14, 1997

[54] PROCESS FOR THE PREPARATION OF TRICYCLIC-HETEROCYCLES

[75] Inventors: Aranapakam M. Venkatesan, Elmhurst; Jay D. Albright, Nanuet, both of N.Y.

[73] Assignee: American Cyanamid Company, Madison, N.J.

[21] Appl. No.: 402,262

[22] Filed: Mar. 10, 1995

Related U.S. Application Data

[62] Division of Ser. No. 287,015, Aug. 8, 1994, Pat. No. 5,436,333.
[51] Int. Cl.⁶ .................. C07D 207/333; C07D 213/26; C07D 333/12
[52] U.S. Cl. .................. 549/71; 549/72; 549/60; 549/484; 549/488; 548/562; 540/586; 540/576; 540/577; 540/578; 540/587
[58] Field of Search .................. 549/60, 72, 71; 548/562

[56] References Cited

PUBLICATIONS

Gronowitz, S. et al. *J. Heterocyclic Chem.* 27, 1159–1160 (1990).
Gronowitz, S. et al. *J. Heterocyclic Chem.* 27, 1127–1129 (1990).
Carey, F. A. et al. *Advanced Organic Chemistry, Part B: Reactions and Synthesis* (Plenum Press, N.Y.), pp. 478–482 (1990).
Carey, F. A. et al., Advanced Organic Chemistry, Part B (New York, Plenum, 1990), pp. 480–481, 689, and 691 Month of Publication Not Provided.
March, J., Advanced Organic Chemistry, Reactions, Mechanisms, and Structures, (New York, Wiley, 1992), pp. 606–608 and 1216 Month of Publication Not Provided.
Negishi, E.–I. –Organometallics in Organic Synthesis (New York, Wiley, 1980), pp. 99 and 404–405 Month of Publication Not Provided.
Renfroe, B. et al., Azepines Part I, Chemistry of Heterocyclic Compounds, vol. 43, (New York, Wiley, 1984), pp. 15, 16, and 68 Month of Publication Not Provided.
Greene, T. W., et al., Protective Groups in Organic Synthesis (New York, Wiley, 1991), pp. 188–191, 265–266, and 270–272 Month of Publication Not Provided.

*Primary Examiner*—Mukund J. Shah
*Assistant Examiner*—King Lit Wong
*Attorney, Agent, or Firm*—Steven R. Eck

[57] ABSTRACT

This invention comprises a process for production of a compound of the formula:

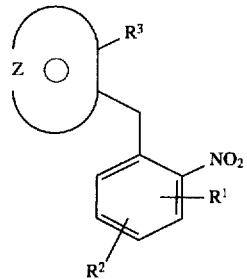

in which
  $R^1$ is selected from the group consisting of H, lower alkyl($C_1$–$C_3$), alkoxy($C_1$–$C_3$), bromo, chloro, fluoro, iodo, —COlower alkyl($C_1$–$C_3$), and —$CF_3$;
  $R^2$ is selected from the group consisting of H, lower alkyl($C_1$–$C_3$), alkoxy($C_1$–$C_3$), amino, bromo, chloro, fluoro, iodo, and —COlower alkyl($C_1$–$C_3$);
  or $R^1$ and $R^2$ taken together are methylenedioxy or ethylenedioxy;
  $R^3$ is an aldehyde or carboxcylic acid moiety;
the moiety

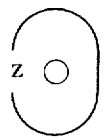

wherein Z represents substituted or unsubstituted phenyl ring or an optionally substituted 5 or 6-membered aromatic heterocyclic ring.

1 Claim, No Drawings

PROCESS FOR THE PREPARATION OF TRICYCLIC-HETEROCYCLES

RELATED APPLICATION

This is a Divisional of U.S. Ser. No. 08/287,015, filed Aug. 8, 1994, now U.S. Pat. No. 5,436,333, by Aranapakam M. Venkatesan and Jay D. Albright.

BACKGROUND OF THE INVENTION

1. Field of the Invention

The present invention relates to a novel process for preparing tricyclic-heterocycles which are useful as intermediates for the preparation of cardio-vascular agents. The tricyclic heterocyclic compounds prepared by this process are useful in treating conditions where decreased vasopressin levels are desired, such as in congestive heart failure, and in other disease conditions characterized by excess renal water reabsorption, and in conditions with increased vascular resistance and coronary vasoconstriction.

2. Background of the Invention

Vasopressin is released from the posterior pituitary either in response to increased plasma osmolarity detected by brain osmoreceptors or decreased blood volume and blood pressure sensed by low-pressure volume receptors and arterial baroreceptors. The hormone exerts its actions through two well defined receptor subtypes: vascular $V_1$ and renal epithelial $V_2$ receptors. Vasopressin-induced antidiuresis, mediated by renal epithelial $V_2$ receptors, helps to maintain normal plasma osmolarity, blood volume and blood pressure.

Vasopressin is involved in some cases of congestive heart failure where peripheral resistance is increased. $V_1$ antagonists may decrease systemic vascular resistance, increase cardiac output and prevent vasopressin induced coronary vasoconstriction. Thus, in conditions with vasopressin induced increases in total peripheral resistance and altered local blood flow, $V_1$-antagonists may be therapeutic agents. $V_1$ antagonists may decrease blood pressure, and thus be therapeutically useful in treatment of some types of hypertension.

The blockade of $V_2$ receptors is useful in treating diseases characterized by excess renal reabsorption of free water. Antidiuresis is regulated by the hypothalamic release of vasopressin (antidiuretic hormone) which binds to specific receptors on renal collecting tubule cells. This binding stimulates adenylyl cyclase and promotes the cAMP-mediated incorporation of water pores into the luminal surface of these cells. $V_2$ antagonists may correct the fluid retention in congestive heart failure, liver cirrhosis, nephrotic syndrome, central nervous system injuries, lung disease and hyponatremia.

Elevated vasopressin levels occur in congestive heart failure which is more common in older patients with chronic heart failure. In patients with hyponatremic congestive heart failure and elevated vasopressin levels, a $V_2$ antagonist may be beneficial in promoting free water excretion by antagonizing the action of antidiuretic hormone. On the basis of the biochemical and pharmacological effects of vasopressin, antagonists of vasopressin, which may be made in accordance with the process of this invention, are expected to be therapeutically useful in the treatment and/or prevention of hypertension, cardiac insufficiency, coronary vasospasm, cardiac ischemia, renal vasospasm, liver cirrhosis, congestive heart failure, nephrotic syndrome, brain edema, cerebral ischemia, cerebral hemorrhage-stroke, thrombosis-bleeding, abnormal states of water rententioin.

Premature birth can cause infant health problems and mortality and a key mediator in the mechanism of labor is the peptide hormone oxytocin. On the basis of the pharmacological action of oxytocin, antagonists of this hormone are useful in the prevention of preterm labor, B. E. Evans et al., J. Med. Chem. 35, 3919 (1992), J. Med. Chem. 36, 3993 (1993) and references therein. The compounds made by the process of this invention are antagonists of the peptide hormone oxytocin and are useful in the control of premature birth.

The present invention relates to a novel process to prepare tricyclic derivatives which exhibit antagonist activity at $V_1$ and/or $V_2$ receptors and exhibit in vivo vasopressin antagonist activity. The compounds also exhibit antagonists activity of oxytocin receptors.

SUMMARY OF THE INVENTION

The invention provides a novel process for the preparation of tricyclic-heterocycles which may be represented by the following structural formula I:

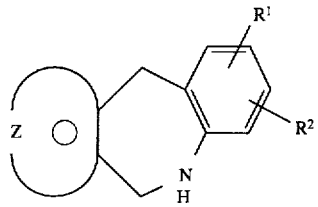

wherein $R^1$ is selected from the group consisting of H, lower alkyl($C_1$–$C_3$), alkoxy($C_1$–$C_3$), amino, bromo, chloro, fluoro, iodo, —COlower alkyl($C_1$–$C_3$), and —$CF_3$; $R^2$ is selected from the group consisting of H, lower alkyl($C_1$–$C_3$), alkoxy($C_1$–$C_3$), bromo, chloro, fluoro, iodo, and —COlower alkyl($C_1$–$C_3$); $R^1$ and $R^2$ taken together may also be methylenedioxy or ethylenedioxy;

the moiety

represents: (1) phenyl or substituted phenyl optionally substituted by one or two substituents selected from ($C_1$–$C_3$)lower alkyl, halogen, ($C_1$–$C_3$)lower alkoxy, or ($C_1$–$C_3$)lower dialkylamino; (2) a 5-membered aromatic (unsaturated) heterocyclic ring having one heteroatom selected from O, N, or S; (3) a 6-membered aromatic (unsaturated) heterocyclic ring having one nitrogen atom; (4) a 5 or 6-membered aromatic (un-saturated) heterocyclic ring having two nitrogen atoms; (5) a 5-membered aromatic (unsaturated) heterocyclic ring having one nitrogen atom together with either one oxygen or one sulfur atom; wherein the 5 or 6-membered heterocyclic rings are optionally substituted by ($C_1$–$C_3$)lower alkyl, halogen or ($C_1$–$C_3$)lower alkoxy. For example, the fused heterocyclic ring may be represented by furan, pyrrole, pyrazole, thiophene, thiazole, oxazole, imidazole, pyrimidine or pyridine ring which may be substituted or unsubstituted. In accordance with the invention, the foregoing compounds are prepared by reacting a tri-n-butyltin aryl or heteroaryl intermediate having a masked aldehyde or carboxylic acid substituent with a methyl-bromo-nitrophenyl intermediate followed by demasking, reduction and cyclization to form the final tricyclic compounds.

DETAILED DESCRIPTION OF THE INVENTION

The process of the present invention are described in the following reaction schemes.

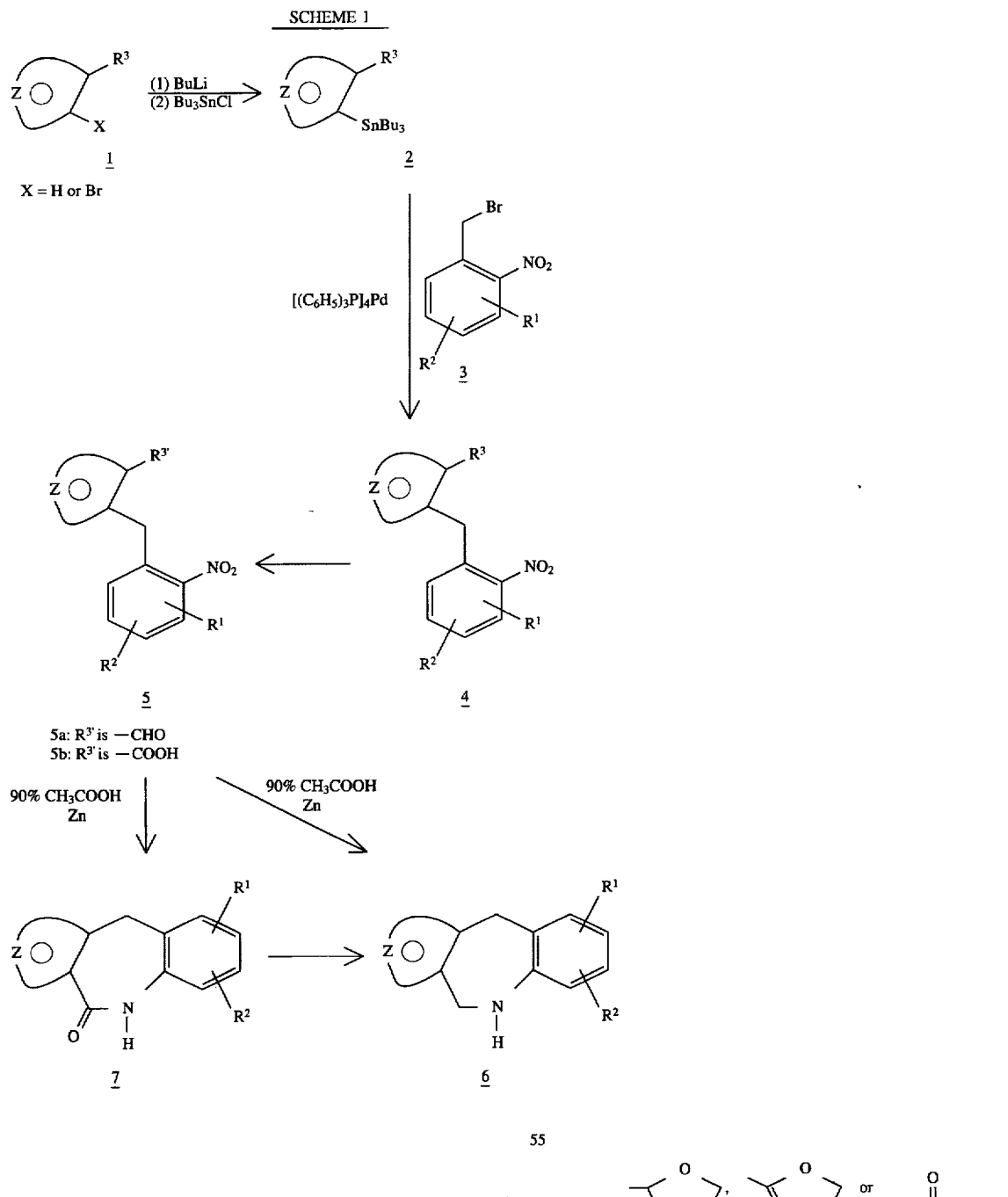

In accordance with the reaction Scheme 1 cyclic substituted intermediate 1, where Z is as described above, X is hydrogen or bromine; and $R^3$ is a masked aldehyde or carboxylic acid moiety, is reacted with n-butyl lithium followed by tri-n-butyltin chloride to give tri-n-butyl tin intermediate 2. $R^3$ may be any suitable masked aldehyde or carboxylic acid moiety such as those selected from moieties of the formulae:

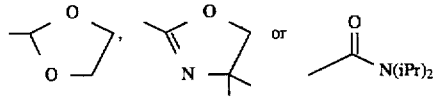

The tri-n-butyl tin intermediate 2 is reacted with compounds of formula 3 where $R^1$ and $R^2$ are described above, in the presence of a palladium catalyst such as tetrakis(triphenylphosphine)palladium (O) to give the nitro intermediate 4. Hydrolysis of intermediate 4 where $R^1$, $R^2$ and Z are defined above, and $R^3$ is a masked aldehyde moiety such as:

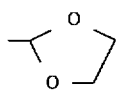

with aqueous acetic acid gives aldehyde intermediate 5a. Further reaction of aldehyde intermediate 5a with zinc in aqueous acetic acid effects reduction and cyclization to give the desired tricyclic-heterocycle 6.

Hydrolysis of intermediate 4 where $R^1$, $R^2$ and Z are defined above and $R^3$ is a masked carboxylic acid moiety such as:

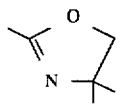

with aqueous acetic acid affords carboxylic acid 5b which is followed by reduction of the nitro group to give the corresponding amine and in situ cyclization to give the lactam 7. Reduction of lactam 7 gives the desired tricyclic-heterocycle 6.

Hydrolysis of intermediate 4 where $R^1$, $R^2$ and Z are defined above and $R^3$ is a moiety of the formula:

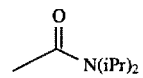

with aqueous sodium hydroxide also affords carboxylic acid 5b which is followed by reduction of the nitro group to give the corresponding amine and in situ cyclization to give the lactam 7. Reduction of lactam 7 gives the desired tricyclic-heterocycle 6.

The reduction of the lactam 7 may be carried out with lithium aluminum hydride(LAH) or similar reagents known to reduce amide carbonyl groups. The lactam 2 may also be reduced by diborane and the diborane-dimethyl sulfide reagent. The conditions for reduction are chosen so as to be compatible with other functional groups in the lactam 7.

The process of the present invention is further illustrated by the particular embodiments set forth in the following Schemes 2–4 where specific masked aldehyde and carboxylic acid starting materials are utilized. It is understood, however, that other equivalent masked aldehyde or carboxylic acid moieties may be substituted as known in the art.

SCHEME 2

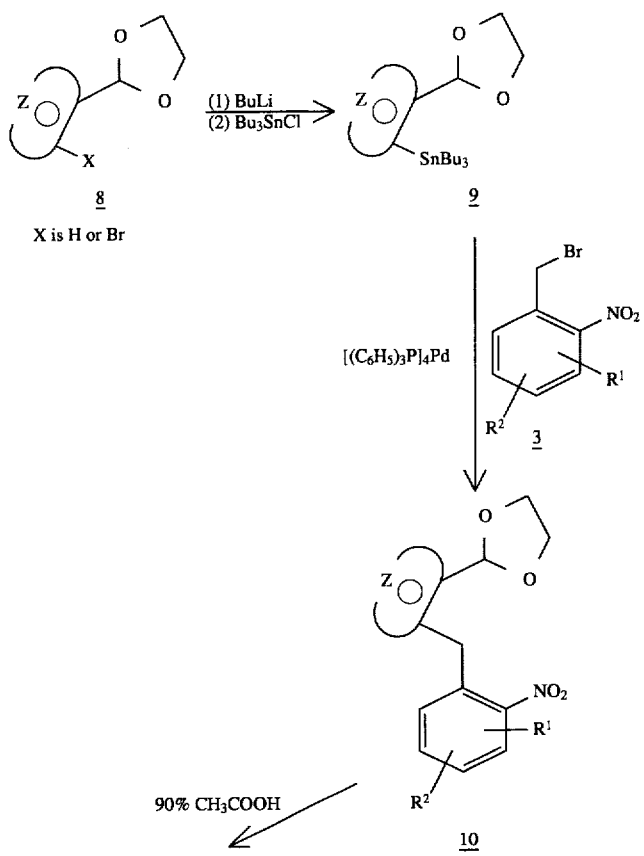

-continued
SCHEME 2

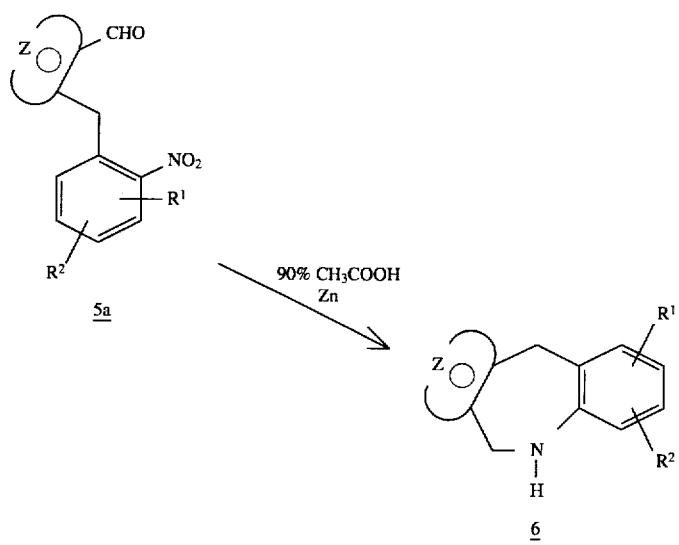

In accordance with the reaction Scheme 2, a dioxolane 8, where Z is as described above and X is hydrogen or bromine, is reacted with n-butyl lithium followed by tri-n-butyltin chloride at −78° to −70° C. to give tri-n-butyl tin intermediate 9.

The tri-n-butyl tin intermediate 9 is reacted with compounds of formula 3 where $R^1$ and $R^2$ are described above, in the presence of tetrakis(triphenylphosphine)palladium (O) in toluene at reflux for about 16 hours to give the nitro intermediate 10. Hydrolysis of intermediate 10 where $R^1$, $R^2$ and Z are defined above, with 80–90% acetic acid at 50°–60° C. gives aldehyde intermediate 5a. Further reaction of intermediate 5a with zinc in 80–90% acetic acid effects reduction and cyclization to give the desired tricyclic-heterocycle 6. The hydrolysis and the reductive cyclization can be carried out in one step by directly reacting the intermediate fill with 90% acetic acid and zinc dust.

SCHEME 3

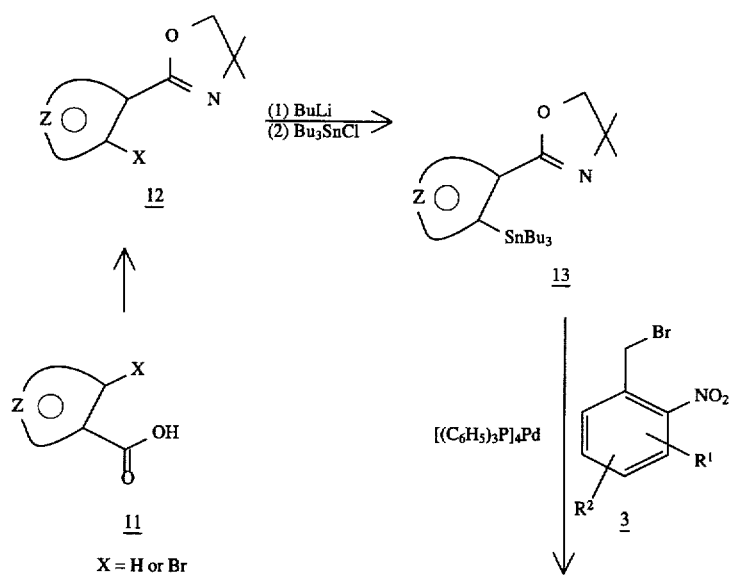

-continued
SCHEME 3

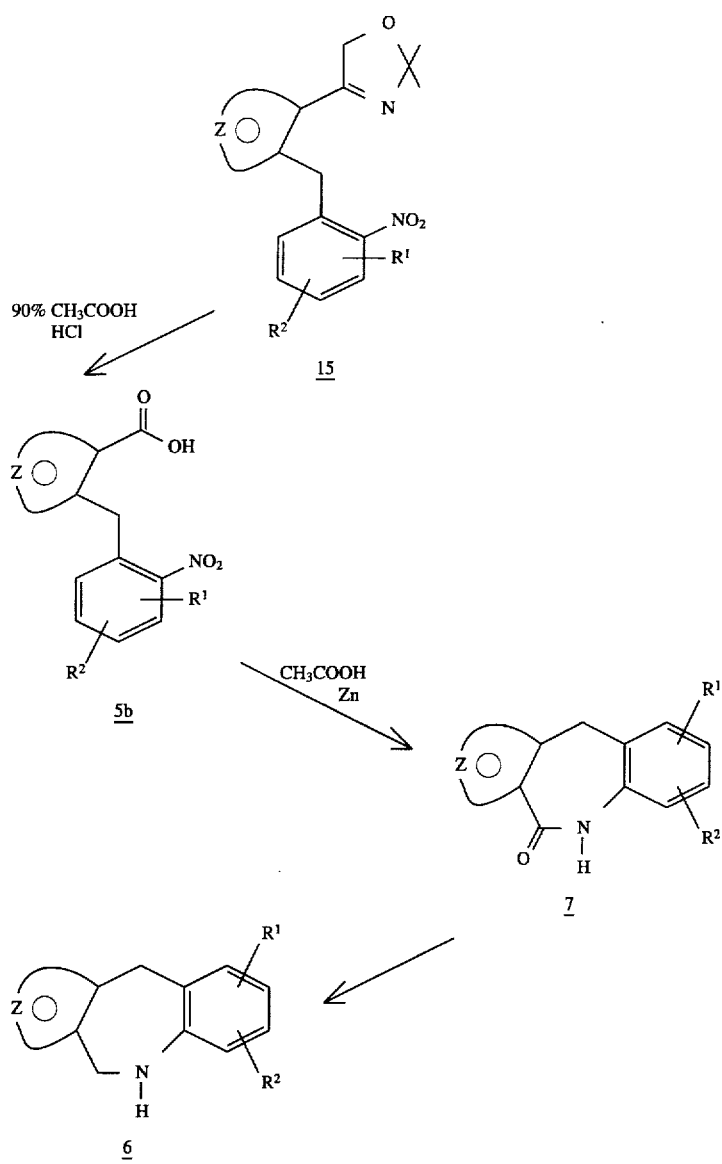

As shown in Scheme 3, carboxylic acid 11, where Z is as described above and X is hydrogen or bromine, is converted to oxazoline 12. Reaction of 12 with n-butyl lithium followed by tri-n-butyltin chloride gives tri-n-butyl tin intermediate 13.

The tri-n-butyl tin intermediate 13 is reacted with compounds of formula 3 where $R^1$, $R^2$ and Z are defined above, in the presence of tetrakis(triphenylphosphine)palladium (O) to give nitro-phenyl intermediate 15. Hydrolysis of intermediate 15 with 80–90% acetic acid affords carboxylic acid 5b which is followed by reduction of the nitro group with zinc in 80–90% acetic acid and cyclisation to give the lactam 2. Reduction of lactam 7 gives the desired tricyclic-heterocycle 6.

As shown in Scheme 4, amide 16 is reacted with n-butyl lithium followed by tri-n-butyltin chloride to give the tri-n-butyl tin intermediate 17.

The tri-n-butyl tin intermediate 17 is reacted with compounds of formula 3 where $R^1$, $R^2$ and Z are defined above, in the presence of a palladium (O) catalyst such as tetrakis(triphenylphosphine)palladium (O) to give nitro-phenyl intermediate 18. Hydrolysis of intermediate 18 with a suitable base such as sodium hydroxide affords carboxylic acid 5b which is followed by reduction of the nitro group with zinc in 80–90% acetic acid to give the desired lactam 7. Reduction of lactam 7 gives the desired tricyclic-heterocycle 6.

In Scheme 1, reduction of the nitro group of compound 5 may be carded out by known methods of reduction such as hydrogenation in the presence of a catalyst such as Pd/C or by chemical reduction such as $SnCl_2$ in ethanol. For Schemes 3 and 4, the nitro group of compound 5b may also be reduced by hydrazine and Pd/C in refluxing ethanol. The reduction conditions are chosen so that they are compatible with other functional groups in the intermediate nitro compound.

SCHEME 4
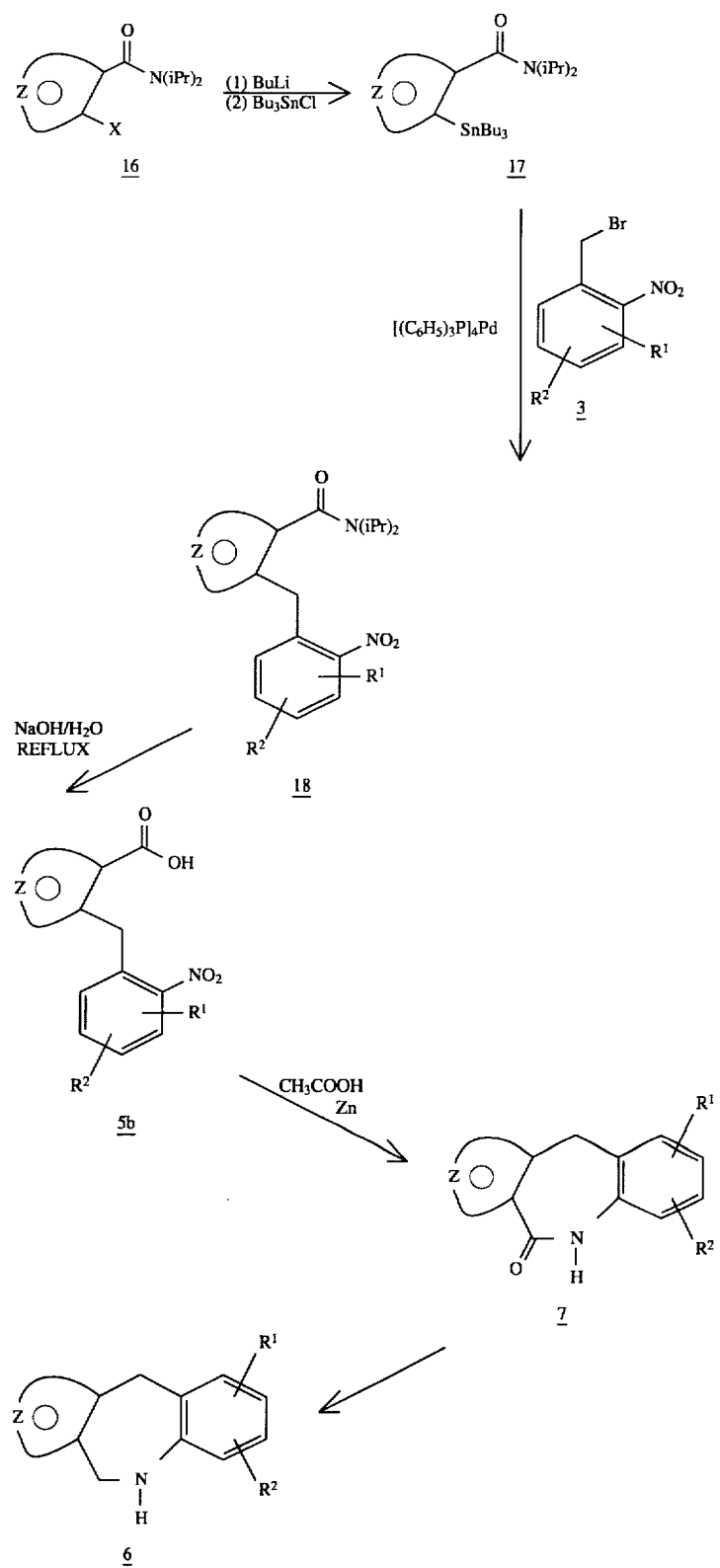

The following non-limiting examples illustrate the process of the present invention.

EXAMPLE 1

2-[2-Tributylstannyl)-3-thienyl]-1,3-dioxolane

To a stirred solution of 15.6 g of 2-(3-thienyl)-1,3-dioxolane in 100 ml of anhydrous ether is added dropwise 74.3 ml of 1.48N n-butyllithium under nitrogen at room temperature. After 15 minutes at reflux, the reaction mixture is cooled to −78° C. and 34.18 g of tri-n-butyltin chloride in 100 ml of dry tetrahydrofuran is added dropwise. After the addition is complete, the mixture is warmed to room temperature and the solvent is evaporated in vacuo to an oily residue. To the residue is added 100 ml of hexane and the resulting precipitate of lithium chloride collected. The filtrate is concentrated in vacuo to a residue which is distilled at 160°/0.04 mm Hg to give 34.16 g of the desired product.

EXAMPLE 2

2-[(2-Nitrophenyl)methyl]-3-thienyl]-1,3-dioxolane

A mixture of 8.8 g of the product of Example 1, 4.5 g of o-nitrobenzyl bromide and 200 mg of tetrakis(triphenylphosphine)-palladium(O) is refluxed in degassed toluene for 16 hours under a nitrogen atmosphere. The reaction mixture is cooled to room temperature and filtered through diatomaceous earth. The toluene is evaporated in vacuo to a residue which is purified by column chromatography on silica gel by elution with 30% ethyl acetate-hexane to give 4.5 g of the desired product as a viscous liquid, $M^+=292$.

EXAMPLE 3

4,10-Dihydro-5H-thieno[3,2-c][1]benzazepine

A solution of 4.0 g of the product of Example 2 in 50 ml of acetone and 50 ml of 90% acetic acid is heated to 60° C. with stirring followed by the slow addition of 10.0 g of zinc dust. Stirring is continued for 6 hours. The reaction mixture is filtered, the collected solids washed with acetone and the combined filtrates concentrated in vacuo to a residue. The residue is extracted with chloroform, which is washed with water. The organic layer is dried with sodium sulfate, filtered and concentrated in vacuo to a residue which is purified by column chromatography on silica gel using 20% ethyl acetate-hexane to give 2.0 g of the desired product as pale yellow crystalline solid, m.p. 86° C., $M^+=202$.

EXAMPLE 4

4,5-Dihydro-4,4-dimethyl-2-[3-(tributylstannyl]-2-thienyl-oxazole

To a solution of 4.5 g of 4,5-dihydro-4,4-dimethyl-2-(2-thienyl)-oxazole in 200 ml of anhydrous ether at −70° C. is added 11 ml of a 2.5M solution of n-butyl lithium in hexane, dropwise under a nitrogen atmosphere. The reaction mixture is stirred at −78° C. for 45 minutes and 8.3 g of tri-n-butyltin chloride in dry ether added dropwise. The reaction mixture is stirred at room temperature for 1 hour and quenched with water. The reaction mixture is extracted with ether, washed with water, dried over sodium sulfate and concentrated in vacuo to an oily residue.

EXAMPLE 5

2-[[3-(2-Nitrophenylmethyl)]-2-thienyl]-oxazole

A solution of the product of Example 4 is mixed with 5.5 g of p-nitrobenzyl bromide in 100 ml of toluene in the presence of 200 mg of tetrakis (triphenylphosphine)-palladium (O) and refluxed for 16 hours. The reaction mixture is cooled to room temperature and filtered. The filtrate is evaporated in vacuo to an oily residue which is purified by column chromatography on silica gel by elution with 30% ethyl acetate-hexane to give 5.7 g of the desired product, $M^+=316$.

EXAMPLE 6

9,10-Dihydro-4H-thieno[2,3-c][1]-benzazepin-10-one

A mixture of 5.0 g of the product of Example 5 in 100 ml of 3:1 acetone-water containing 30 ml of 1N HCl is refluxed for 24 hours. The reaction mixture is concentrated in vacuo to a residue which is dissolved in 100 ml of glacial acetic acid. The mixture is stirred at 70° C. while 10.0 g of zinc dust is slowly added. Stirring is continued for 6 hours. The reaction mixture is cooled to room temperature and filtered. The filtrate is evaporated in vacuo to a residue which is extracted with chloroform. The organic layer is dried over sodium sulfate and concentrated in vacuo to give 2.9 g of the desired product as a brown solid, $M^+=215$.

EXAMPLE 7

9,10-Dihydro-4H-thieno[2,3-c][1]benzazepine

A stirred solution of 2.0 g of the product of Example 6 and 500 mg of lithium aluminum hydride in 200 ml of tetrahydrofuran is refluxed for 4 hours. The reaction mixture is carefully quenched with ice cold water and extracted with chloroform. The organic layer is washed well with water, dried over anhydrous sodium sulfate, filtered and concentrated in vacuo to a residue. The residue is purified by column chromatography on silica gel by elution with 30% ethyl acetate-hexane to give 1.2 g of the desired product as a bright yellow solid, $M^+=202$.

What is claimed is:

1. A process for production of a compound of the formula:

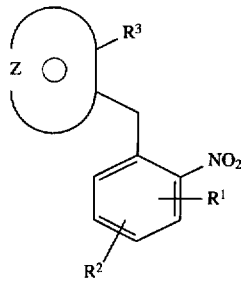

in which $R^1$ is selected from the group consisting of H, lower alkyl($C_1$-$C_3$), alkoxy($C_1$-$C_3$), bromo, chloro, fluoro, iodo, —COlower alkyl($C_1$-$C_3$), and —$CF_3$;

$R^2$ is selected from the group consisting of H, lower alkyl($C_1$-$C_3$), alkoxy($C_1$-$C_3$), amino, bromo, chloro, fluoro, iodo, and —COlower alkyl($C_1$-$C_3$);

or $R^1$ and $R^2$ taken together are methylenedioxy or ethylenedioxy;

$R^3$ is an aldehyde or carboxylic acid moiety; and the moiety

represents: (1) a 5-membered aromatic (unsaturated) heterocyclic ring having one heteroatom selected from O, N, or S; (2) a 6-membered aromatic (unsaturated) heterocyclic ting having one nitrogen atom; (3) a 5 or 6-membered aromatic (unsaturated) heterocyclic ring having having two nitrogen atoms; or (4) a 5-membered aromatic (unsaturated) heterocyclic ting having one nitrogen atom together with either one oxygen or one sulfur atom; wherein the 5 or 6-membered heterocyclic rings are optionally substituted by $(C_1-C_3)$lower alkyl, halogen or $(C_1-C_3)$lower alkoxy;

the process comprising reacting a compound of the formula:

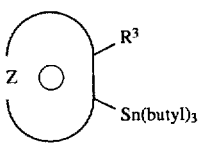

with a compound of the formula:

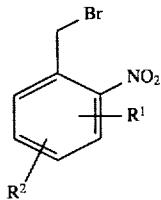

in the presence of a palladium (O) catalyst.

* * * * *